United States Patent [19]

Amselem

[11] 4,080,447
[45] Mar. 21, 1978

[54] THERAPEUTIC COMPOSITION HAVING AN INHIBITING ACTIVITY ON BLOOD PLATE AGGREGATION

[75] Inventor: Armand Amselem, Toulouse, France

[73] Assignee: Centre d'Etudes pour l'Industrie Pharmaceutique, Toulouse, France

[21] Appl. No.: 671,496

[22] Filed: Mar. 29, 1976

[30] Foreign Application Priority Data

Apr. 18, 1975 France .................................. 75 12084

[51] Int. Cl.$^2$ .......................................... A61K 31/625
[52] U.S. Cl. .................................................. 424/232
[58] Field of Search ................................ 424/230, 232

[56] References Cited

FOREIGN PATENT DOCUMENTS 7,303,503  2/1973  France.

OTHER PUBLICATIONS

Chem. Abst. (1) 77 – 14689 H, (1972).
Chem. Abst. (2)78 – 118993q, (1973).

Primary Examiner—Stanley J. Friedman
Attorney, Agent, or Firm—Young & Thompson

[57] ABSTRACT

This invention relates to a therapeutic composition comprising, as active ingredient, a combination of 5-(2-chloro-benzyl)-4,5,6,7-tetrahydro-thieno[3,2-c]-pyridine and acetylsalicylic acid, the components of the combination being both present in the free state or as a pharmacologically acceptable salt. Said composition is useful both preventively and curatively for the treatment of thrombo-embolic diseases.

8 Claims, No Drawings

THERAPEUTIC COMPOSITION HAVING AN INHIBITING ACTIVITY ON BLOOD PLATE AGGREGATION

This invention relates to a therapeutic composition having an inhibiting activity on blood plate aggregation comprising, as active ingredient, a combination of 5-(2-chloro-benzyl)-4,5,6,7-tetrahydro-thieno[3,2-c]-pyridine (or ticlopidine) and acetyl salicylic acid (or aspirin), the components of the combination being both present in the free state or as a pharmacologically acceptable salt.

Ticlopidine was previously described in French patent application N° P.V. 73,03503, filed Feb. 1st, 1973; it has the following structural formula:

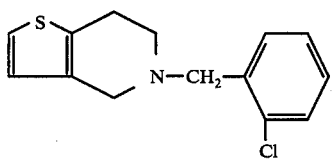

Ti clopidine, and its pharmacologically acceptable salts, have pharmacologically useful inhibiting properties on blood plate aggregation.

Acetylsalicylic acid and its non-toxic salts have long been known for their antalgic, anti-inflammatory and antithermic pharmacological properties. Recently, it was found that aspirin is capable of modifying blood plate aggregation by inhibiting same, preventing the formation of blood-plate aggregates which are responsible for arterial thromboses.

According to the invention, it has now been found that, in the presence of acetylsalicylic acid, ticlopidine has a markedly superior hemodynamic activity, both qualitatively and quantitatively.

This action is apparent from the results of the pharmacological and clinical investigation reported below together with the toxicological investigation.

I. TOXICOLOGICAL INVESTIGATION

Said investigation related to:

(1) The acute toxicity of ticlopidine, of aspirin and of the combination of this invention: in white Swiss strain mice, the $LD_{50}/72$ hours was found to be 2.3 g/kg in the case of ticlopidine, 1.1 g/kg in the case of aspirin, and 1.8 g/kg in the case of the combination of this invention in a ratio of 1 g ticlopidine for 2 g aspirin; in white Wistar strain rats, the $LD_{50}/72$ hours was found to be in excess of 4 g/kg in the case of ticlopidine, 1.5 g/kg in the case of aspirin and 2.7 g/kg in the case of the combination of this invention in a ratio of 1 g ticlopidine for 2 g aspirin;

(2) The chronic toxicity;
(3) The delayed toxicity;
(4) The local and systemic tolerance.

It is found that the composition of this invention is well tolerated, under the conditions used for the experiments in animals, whether on oral, parenteral or rectal administration, without causing any local or systemic intolerance reactions. Similarly, investigation of the acute toxicity of the composition provided no evidence of synergistic toxicity but, on the contrary, a decrease of the $LD_{50}$.

II PHARMACOLOGICAL INVESTIGATION

Said investigation related to the inhibiting activity on blood plate aggregation of the composition of this invention.

1. Experimental procedure

Wistar strain rats, having a body weight of not less than 400 g, are fasted 24 hours prior to the test, while being maintained under slight anesthesia with diethyl ether. A jugular vein is exposed after incision of the skin and dissection of the subcutaneous tissues.

The venous puncture is effected by means of a 5 ml Plastipak B.D. type syringe with a BD 19 G 1 1/4 needle and containing 0.32 ml sodium citrate solution. Blood is taken until the 3 ml mark is attained.

Mixing is insured by tumbling over the syringe 3 times in succession and the citrate containing blood is immediately transferred to a polyethylene or silicone glass hemolysis tube.

A first centrifugation is effected at 100 g during 30 minutes; it gives a platelet-rich plasma (P.R.P.) a portion of which is collected. A second centrifugation is effected at 600 g during 20 minutes; it provides a plasma having a low platelet content (P.P.P.)

The platelet concentrations are determined in the P.R.P. and the P.P.P. by means of a Coulter type apparatus. A suitable mixture of both plasmas provides a plasma containing $600,000 \pm 20,000$ platelets per $mm^3$; the plasma thus reconstituted will be used in all aggregation determinations.

1.1. Determination of ADP-induced blood plate aggregation 0.4 ml plasma are placed in a siliconized tube provided with a bar magnet, also siliconized. The tube is introduced in a Bryston type aggregometer connected to an optical density variation recorder.

The thermostat-controlled bath is maintained at 37° C and the magnetic stirrer is set at 1100 r.p.m.

When, after a suitable period of time, the base line representing plasma transmission has reached a stable value, 0.05 ml of a solution containing 10 μM A.D.P. (adenosine diphosphate) are added. Platelet aggregation induces an increase of light transmission; this is followed by a decrease during the disaggregation stage and, thus, the maximum optical density variation recorded characterizes the extent of the aggregation.

1.2. Determination of collagen-induced blood plate aggregation

The above procedure is used, except that the A.D.P solution is substituted with 0.05 ml of a collagen suspension ($E_{420} = 0.27$) (bovine tendon extract). The resulting aggregation is characterized by the value of the initial velocity of the phenomenon, measured by the slope, at the beginning of the curve, expressed as $\Delta D.O./mn$.

2. Results 2.1. Collagen-induced aggregation (initial aggregation velocity $\Delta D.O./mn$)

Three groups of animals were used, each group comprising 20 rats.

The first group was administered 100 mg/kg ticlopidine, by gastric intubation; the second group was administered 100 mg/kg aspirin, under the same experimental conditions; and the third group was administered 100 mg tichlopidine + 100 mg aspirin.

The experimental results obtained are given in Table I.

TABLE I

| Treatment | Velocity before treatment (control) | After treatment | | | | | | | |
|---|---|---|---|---|---|---|---|---|---|
| | | 1 hour* | | 2 hours | | 3 hours | | 4 hours | |
| | | velocity | I% | velocity | I% | velocity | I% | veocity | I% |
| Ticlopidine | 0.150 | 0.110 | 26.7 | 0.005 | 96.7 | 0.008 | 94.5 | 0.015 | 90.0 |
| Aspirin | 0.170 | 0.035 | 74.9 | 0.008 | 95.3 | 0.015 | 89.4 | 0.030 | 82.4 |
| Ticlopidine + Aspirin | 0.160 | 0.003 | 98.1 | 0.002 | 98.8 | 0.003 | 98.1 | 0.005 | 96.9 |

*I% = percent inhibition 2.2. A.D.P.-induced aggregation ($\Delta DO$ max = maximum aggregation)

The same experimental procedure is used, group I being administered (gastric intubation) 100 mg ticlopidine/kg, group II being administered 100 mg aspirin/kg and group III being administered 100 mg ticlopidine + 100 mg aspirin/kg.

The results obtained are given in Table II. It is apparent from said results that, whatever method is used for the determination of blood-plate aggregation (with A.D.P. or with collagen), the composition of this invention exhibits potentiated inhibiting properties on blood plate aggregation, with respect to its individual components; at the dosages used in the above tests, the synergy is predominantly apparent from the extension of the anti-aggregation effects: the anti-aggregation effects are superior to the sum of the activity inherent to ticlopidine and of that inherent to aspirin.

TABLE II

| Treatment | Before treatment $\Delta DOmax$ (control) | After treatment | | | | | | | |
|---|---|---|---|---|---|---|---|---|---|
| | | 1 hour | | 2 hours | | 3 hours | | 4 hours | |
| | | $\Delta DOmax$ | I% | $\Delta DOmax$ | I% | $\Delta DOmax$ | I% | $\Delta DOmax$ | I% |
| Ticlopidine | 0.165 | 0.115 | 30.3 | 0.080 | 51.5 | 0.090 | 45.5 | 0.120 | 27.3 |
| Aspirin | 0.185 | 0.180 | 2.7 | 0.190 | −2.7 | 0.178 | 3.8 | 0.183 | 1.1 |
| Ticlopidine + Aspirin | 0.170 | 0.070 | 58.8 | 0.060 | 64.7 | 0.065 | 61.8 | 0.080 | 52.9 |

III. CLINICAL TESTS

The results obtained in laboratory animals made it possible to test the composition of this invention in humans.

1. Experimental procedure
1.1. Determination of blood plate aggregation
1.1.1. Principle The method comprises the in vitro determination of blood plate aggregation, in the presence of various aggregation-inducing agents.

1.1.2. Collection of blood samples

Blood is taken by direct venous puncture with a plate-bearing needle. Use of a syringe should be avoided. The blood is collected in a plastic tube, over 3.8% sodium citrate, in a ratio of 1/10.

1.1.3. Preparation of a mixture having optimum platelet concentration

The blood is centrifuged at 1500 r.p.m. during 10 minutes; the supernatant is decanted by means of an unwettable device.

The resulting sediment is again centrifuged at 3000 r.p.m. during 30 minutes, to give a plasma having a low platelet content (P.P.P.).

The platelets contained in the supernatant from the first centrifugation are counted. Suitable dilution of the supernatant is effected with the P.P.P., to give a plasma containing from 200,000 to 300,000 platelets/mm$^3$, this mixture representing the platelet-rich plasma (P.R.P.).

1.1.4. Determination of the aggregation

The determination is effected in an aggregometer [photometer, the thermostatically controlled cells of which (37° C) contain a bar magnet stirred at constant speed (1100 r.p.m.)].

In view of the optical density differences observed from one plasma to the other, it is necessary to calibrate the photometer between two terminals: one is obtained by adding 0.3 ml P.R.P. in a cell containing a bar magnet, and adding thereto a volume of buffer equal to the volume of solution which will contain the aggregation-inducing agent. The other is obtained with 0.3 ml P.P.P. to which is added an identical volume of buffer. The determination is carried out with a cell containing 0.3 ml P.R.P. heated to 37° C to which is added the solution of aggregation-inducing agent. Some authors use one volume of solution containing the aggregation-inducing agent in 0.1 ml, others, a much smaller volume.

1.1.5. Aggregation-inducing agents used
1.1.5.1. A.D.P.

ADP is a physiological mediator involved in blood plate aggregation.

1.1.5.2. Collagen

A veal tendon extract, collagen, is available in freeze-dried condition. It will keep for about two months, after rehydration. To be diluted and incubated at the time of use, at 37° C, during a period of time which varies with each batch.

1.1.6. Analysis of the resulting curves
1.1.6.1. ADP

Different ADP concentrations are used. At low concentrations (0.1–1 $\mu M$), ADP induces a reversible aggregation. At intermediate concentrations (1–3 $\mu M$), there may be observed an aggregation induced by the added ADP (exogenous ADP) followed by partial disaggregation and by a secondary reaggregation, the latter being due to the release of ADP contained in these platelets (endogenous ADP): this is the so-called "double-wave" phenomenon.

At high ADP concentrations (3-10 μM), a single aggregation wave is observed, due to the mergence of the two preceding phenomena.

The standard procedure involves preparing different ADP concentrations (0.5, 1, 2, 5 and 10 μM). The phenomenon is characterized by the maximum transmission obtained during aggregation, the apparatus being set in such a manner that 100% corresponds to P.P.P. and 0% to P.R.P.

1.1.6.2. Collagen

A single concentration is used. A latency stage exists, obtained on aggregation, after which the platelets release ADP and induce blood plate aggregation. The following are determined:

$\theta_1$(mn) = latency time on aggregation
$\theta_3$(mn) = half-aggregation time
$\lambda$ = maximum percent aggregation 1.2. Investigative procedure:

Mr. Pierre D . . . was administered, twice daily, during 7 successive days, two 250 mg aspirin tablets; the following week, he was administered daily, during 7 successive days, the composition of this invention as tablets containing each 250 mg aspirin and 125 mg ticlopidine. In other words, Mr. D . . . was administered, during the first week, 1 g aspirin per day and, during the second week of treatment, 1 g aspirin + 0.500 g ticlopidine per day. Mr. Jean R . . . was treated in an identical manner, the test materials, however, being administered in the reverse order. Thus, Mr R . . . was administered, during the first week, 0.500 g ticlopidine per day and, during the second week of treatment, 1 g aspirin + 0.500 g ticlopidine per day.

1.3. Results

The results of the blood-plate aggregation tests are tabulated in following Table III.

TABLE III

| Subject | Determination Time | Percent aggregation | | | | | | | |
|---|---|---|---|---|---|---|---|---|---|
| | | Test with A.D.P. | | | | | Test with collagen | | |
| | | 0.5μM | 1μM | 2μM | 5μM | 10μM | $\theta_1$ | $\theta_3$ | $\lambda$ |
| Mr. Pierre D.. | Time 0 | 20 | 70 | 80 | 83 | 81 | 1.2 | 1.9 | 68 |
| | + 7 days | 28 | 54 | 69 | 74 | 78 | 1.8 | 3.3 | 60 |
| | + 14 days | 10 | 21 | 33 | 50 | 53 | no aggregation | | |
| Mr Jean R.. | Time 0 | 12 | 31 | 46 | 70 | 74 | 1.4 | 2.1 | 61 |
| | + 7 days | 14 | 24 | 30 | 49 | 60 | 1.4 | 2.1 | 58 |
| | + 14 days | 8 | 15 | 20 | 36 | 44 | no aggregation | | |

The following facts are apparent from the above results: Mr. Pierre D . . . who was administered, during the first week, aspirin only and, during the second week, the composition of this invention:

is sparingly receptive to the inhibiting activity of aspirin, because the test results show there is practically no significant variation of ADP-induced aggregation and there is moderate inhibition of collagen-induced aggregation, relating to the aggregation kinetics, is highly receptive to the inhibiting activity of the composition of this invention which has a clear effect on ADP-induced aggregation and which produces a collapse of collagen-induced aggregation.

Mr. Jean R . . . who was administered, during the first week, ticlopidine only and, during the second week, the composition of this invention:

is sparingly receptive to the inhibiting activity of ticlopidine, said inhibiting being moderately significant on ADP-induced aggregation and nil in the test with collagen, is receptive to the inhibiting activity of the composition of this invention, said activity being much higher in the case of ADP and resulting in total inhibition of the collagen-induced aggregation test.

IV. THERAPEUTIC APPLICATIONS

In view of its outstanding inhibiting activity on blood plate aggregation, the composition of this invention is applicable to all diseases which produce a pathological modification of blood plate aggregation, such as thrombo-embolic diseases, for example. Therefore, the composition of this invention may be used both preventively and curatively.

V. PHARMACEUTICAL FORMULATION

In the above applications, the composition is preferably administered by the oral or the rectal route, the active ingredients being combined with the carriers and excipients suitable for such routes of administration. Generally, the aspirin/ticlopidine weight ratio, in the composition of this invention, is greater than 1 and preferably comprised between 2 and 4.

Each unit dose may advantageously contain 0.050-0.7 g ticlopidine and 0.100-0.9 g aspirin, the daily dosage regimen varying from 0.050 g to 2 g ticlopidine and from 0.100 g to 4 g aspirin.

Non-limiting Examples of pharmaceutical formulations of the composition of this invention are given below.

| 1 - Tablets | |
|---|---|
| Ticlopidine | 0.150 g |
| Aspirin | 0.300 g |
| Maize starch | 0.020 g |
| Magnesium stearate | 0.050 g |
| Talc | 0.050 g |
| Lactose | 0.100 g |

| 2 - Coated tablets | |
|---|---|
| Ticlopidine | 0.100 g |
| Aspirin | 0.200 g |
| Magnesium stearate | 0.050 g |
| Talc | 0.020 g |
| Shellac | traces |
| Gum arabic | 0.010 g |
| Granulated sugar | 0.050 g |
| Titanium dioxide | traces |
| Orange Yellow S | traces |

| 3 - Capsules | |
|---|---|
| Ticlopidine hydrochloride | 0.150 g |
| Aspirin | 0.200 g |
| Talc | 0.010 g |
| Magnesium stearate | 0.010 g |

| 4 - Dosage-bag | |
|---|---|
| Ticlopidine | 0.200 g |
| Aspirin | 0.500 g |
| Talc | 0.050 g |
| Magnesium stearate | 0.200 g |

| 5 - Suppositories | |
|---|---|
| Ticlopidine | 0.050 g |
| Aspirin | 0.200 g |
| Semi-synthetic glycerides, q.s. to make | 3 g for 1 |

| |
|---|
| suppository (adult) |

Having now described our invention what We claim as new and desire to secure by Letters Patent is:

1. Therapeutic composition having an inhibiting activity on blood plate aggregation comprising, as active ingredient, a combination of 5-(2-chloro-benzyl)-4,5,6,7-tetrahydro-thieno-[3,2-c]-pyridine, hereinafter called ticlopidine, and acetylsalicylic acid, hereinafter called aspirin, formulated for the daily administration of 0.050–2 g ticlopidine and 0.100–4 g aspirin, the weight ratio of aspirin to ticlopidine being greater than one and up to four.

2. Therapeutic composition as claimed in claim 1, wherein the active ingredient is combined with a pharmacologically acceptable carrier.

3. Therapeutic composition as claimed in claim 1, wherein each component of the conbination is present in a chemical form selected from the free compound and a pharmacologically acceptable salt thereof.

4. Therapeutic composition having an inhibiting activity on blood plate aggregation comprising, an active ingredient, a combination of 5-(2-chlorobenzyl)-4,5,6,7-tetrahydro-thieno-[3,2-c]-pyridine, hereinafter called ticlopidine, and acetylsalicylic acid, hereinafter called aspirin, in unit dosage form, each unit does containing 0.050–0.7 g ticlopidine and 0.100–0.9 g aspirin, the weight ratio of aspirin to ticlopidine being greater than one and up to four.

5. Therapeutic composition as claimed in claim 4, wherein the active ingredient is combined with a pharmacologically acceptable carrier.

6. Therapeutic composition as claimed in claim 4, wherein each component of the combination is present in a chemical form selected from the free compound and a pharmacologically acceptable salt thereof.

7. Therapeutic composition as claimed in claim 1, wherein said weight ratio is about 1:1.

8. Therapeutic composition as claimed in claim 1, wherein said weight ratio is about 1:2.5.

* * * * *